United States Patent
Kaesemeyer

(12) 
(10) Patent No.: US 6,239,172 B1
(45) Date of Patent: May 29, 2001

(54) FORMULATIONS FOR TREATING DISEASE AND METHODS OF USING SAME

(75) Inventor: Wayne H. Kaesemeyer, Augusta, GA (US)

(73) Assignee: NitroSystems, Inc., Augusta, GA (US)

( * ) Notice: Subject to any disclaimer, the term of this patent is extended or adjusted under 35 U.S.C. 154(b) by 0 days.

(21) Appl. No.: 09/226,580

(22) Filed: Jan. 7, 1999

Related U.S. Application Data

(63) Continuation-in-part of application No. 08/833,842, filed on Apr. 10, 1997, now Pat. No. 5,968,983.

(51) Int. Cl.$^7$ ............................. A01N 43/16; A61K 31/35
(52) U.S. Cl. ............................................................ 514/460
(58) Field of Search ............................................. 514/460

(56) References Cited

U.S. PATENT DOCUMENTS

| | | | |
|---|---|---|---|
| 5,147,650 | 9/1992 | Fregly et al. | 424/439 |
| 5,428,070 | 6/1995 | Cooke et al. | 514/310 |
| 5,543,430 | 8/1996 | Kaesemeyer | 514/565 |
| 5,767,160 | 6/1998 | Kaesemeyer | 514/565 |
| 5,795,898 | 8/1998 | Brown et al. | 514/263 |
| 5,830,879 | 11/1998 | Isner | 514/44 |
| 6,147,109 | 11/2000 | Liao et al. | 514/460 |

FOREIGN PATENT DOCUMENTS

| | | |
|---|---|---|
| WO 99/18952 | 4/1999 | (WO) . |
| WO 99/47153 | 9/1999 | (WO) . |
| WO 00/03746 | 1/2000 | (WO) . |
| WO 00/56403 | 9/2000 | (WO) . |

OTHER PUBLICATIONS

Cuevas, P., Hypotensive Activity of Fibroblast Growth Factor, Science, vol. 254, Nov. 22, 1991, pp. 1208–1210.

Sellke et al., "Enhanced microvascular relaxations to VEGF and bFGF in chronically ischemic porcine myocardium", 271 (2 pt 2) H713–20, Aug. 1996.*

Sunderkotter, C. et al. Macrophages and angiogenesis. J. Leukoc Biol. Mar. 1994, 55(3):410–422.*

Bassenge, E. Coronary Vasomotor Responses: Role of Endothelium and Nitrovasodilators. Cardiovascular Drugs and Therapy 1994; 8:601–610.*

Sellke, F.W. et al. Enhanced Microvascular Relaxations to VEGF and bFGF in Chronically Ischemic Porcine Myocardium. Am. J. Physiol. Aug. 1996;271(2 Pt 2):H713–20.

Sunderkotter, C. et al. Macrophages and angiogenesis. J Leukoc Biol. Mar. 1994; 55(3):410–22.

Metais, C. et al. Effects of coronary artery disease on expression and microvascular response to VEGF. Am J Physiol. Oct. 1998;275(4 Pt. 2):H1411–8.

Murohara, T. et al. Nitric Oxide Synthase Modulates Angiogenesis in Response to Tissue Ischemia. J. Clin. Invest. Jun. 1, 1998; 101(11):2567–78.

Witzenbichler G. et al. Vascular endothelial growth factor–C (VEGF–C/VEGF–2) prmotes angiogenesis in the setting of tissue ischemia. Am J Pathol Aug. 1998: 153(2):381–94.

Ogonowski, A.A. et al. Effect of Nitric Oxide Donors and Synthase Agonists on Uptake of Cellular L–Arginine. Physiobiologist Sep. 1998 (abstract only).

Ogonowski, A.A. et al. Effect of Nitric Oxide Donors and Synthase Agonist Peptides on Endothelial Cell Uptake of L–Arginine. FASEB Journal Mar. 17, 1998; 12 (4): A442 (abstract only).

Jin, L.M. et al. Effects of Acetylcholine and Porstacyclin on Endothelial Cell Transport of L.Arginine. FASEB Mar. 1998 (abstract only).

Bouck, N. et al. How Tumors Become Angiogenic. Advances in Cancer Research 1996; 69:136–174.

* cited by examiner

Primary Examiner—Dwayne C. Jones
(74) Attorney, Agent, or Firm—Benesch, Friedlander, Coplan & Aronoff LLP; Raymond A. Miller

(57) ABSTRACT

A therapeutic mixture comprised of L-arginine and angiogenic growth factors is disclosed for the treatment of diseases related to endothelial dysfunction.

14 Claims, 1 Drawing Sheet

US 6,239,172 B1

FORMULATIONS FOR TREATING DISEASE AND METHODS OF USING SAME

This is a continuation-in-part of U.S. Ser. No. 08/833,842 field Apr. 10, 1997 which issued as U.S. Pat. No. 5,968,983 on Oct. 19, 1999.

BACKGROUND OF THE INVENTION

This invention relates generally to therapeutic formulation comprised of a combination of angiogenic growth factors and substrates of Nitric Oxide Synthase ("NOS"), preferably arginine, as well as a method of treating, preventing and/or ameliorating cardiocerebrorenovascular disease and the symptoms thereof. More particularly, the present invention is directed to the administration of a biological equivalent of arginine and an agonist of NOS (e.g., vascular endothelium growth factor ("VEGF")) to produce a beneficial effect.

DESCRIPTION OF RELATED ART

One approach to treating cardiac disease is to effect the dilation of vascular conduits in the body. In this regard, nitric oxide has been shown to be formed enzymatically as a normal metabolite from arginine in the vascular endothelium and provides an important component to the formation of endothelium-derived relaxing factor (EDRF). EDRF appears to be equivalent to Endothelium Derived Nitric Oxide (EDNO) and as used herein EDRF and EDNO are used interchangeably unless otherwise indicated.

It has also been established that a family of enzymes called Nitric Oxide Synthase ("NOS") form nitric oxide from L-arginine, and the nitric oxide produced is responsible for the endothelium dependent relaxation and activation of soluble guanylate cyclase, neurotransmission in the central and peripheral nervous systems, and activated macrophage cytotoxicity. Nitric Oxide Synthase occurs in many distinct isoforms which include a constitutive form ("cNOS") and an inducible form (iNOS). The constitutive form is present in normal endothelial cells, brain, neurons and some other tissues. Formation of nitric oxide by the constitutive form in endothelial cells is thought to play an important role in normal blood pressure regulation, prevention of endothelial dysfunction such as hyperlipodemia, arteriosclerosis, thrombosis, and restenosis. The by-product of the conversion of L-arginine is L-citrulline. Brain, endothelium, and macrophage isoforms of NOS appear to be products of a variety of genes that have approximately 50% amino acid identity. NOS in brain and in endothelium have very similar properties, the major differences being that brain NOS is cytosolic and the endothelial enzyme is mainly a membrane-associated protein.

Functionally, the constitutive form of Nitric Oxide Synthase, which is the predominant synthase present in brain and endothelium, may be active under basal conditions and can be further stimulated by increases in intracellular calcium that occur in response to receptor-mediated agonists or calcium ionophores. cNOS appears to be the "physiological" form of the enzyme and plays a role in a diverse group of biologic processes. In vitro studies suggest that the activity of NOS can be regulated in a negative feedback manner by nitric oxide itself. In cardiocerebrorenovascular circulation, the primary target for constitutively produced nitric oxide is believed to be soluble guanylate cyclase located in vascular smooth muscle, the myocardium (myocytes) and coronary vascular smooth muscle.

In contrast to the cNOS, the inducible, calcium-independent form, iNOS was initially only described in macrophages. It is now known that induction of nitric oxide synthase can occur in response to appropriate stimuli in many other cell types. This includes both cells that normally do not express a constitutive form of nitric oxide synthase, such as vascular smooth muscle cells, as well as cells such as those of the myocardium that express considerable levels of the constitutive isoform. The inducible form of nitric oxide synthase has been found to be induced in vascular smooth muscle cells, for example, by various cytokines and/or microbial products.

iNOS exhibits negligible activity under basal conditions, but in response to factors such as lipopolysaccharide and certain cytokines, expression occurs over a period of hours. The induced form of the enzyme produces much greater amounts of NO than the constitutive form, and induced NOS appears to be the "pathophysiological" form of the enzyme because high concentrations of NO produced by iNOS can be toxic to cells. Induction of iNOS can be inhibited-by glucocorticoids and some cytokines.

SUMMARY OF THE INVENTION

The term "subject" as used herein to mean any mammal, including humans, where nitric oxide formation from arginine occurs. The methods herein for use on subjects contemplate prophylactic use as well as curative use.

The term endpoints as used herein refers to clinical events encountered in the course of treating cardiovascular disease, up to and including death (mortality).

L-arginine as used herein includes all biochemical equivalents (i.e. salts, precursors, and its basic form). "To mix", "mixing", or "mixture(s)" as used herein means mixing a substrate (i.e. L-arginine) and an agonist (i.e. angiogenic growth factors ): 1) prior to administration ("in vitro mixing"); 2) mixing by simultaneous and/or consecutive, but separate (i.e. separate intravenous lines) administration of substrate (L-arginine) and agonist (angiogenic growth factor) to cause "in vivo mixing"); and 3) the administration of a NOS agonist after saturation with a NOS substrate (i.e. L-arginine is administered to build up a supply in the body prior to administering the NOS agonist (nitroglycerin or angiogenic growth factors)); or any combination of the above which results in the delivery of therapeutic amounts of a NOS agonist and a NOS substrate in an additive or synergistic way with regard to the treatment of disease, preferably cardiocerebrorenovascular disease.

Agonist refers to an agent which stimulates the biotransformation of a substrate such as L-arginine either through enzymatic activation or increasing gene expression (i.e. increased levels of NOS). Of course, either or both of these mechanisms may be acting simultaneously.

The present invention is preferably useful in preventing, treating, arresting, or ameliorating disease conditions which are benefited by the bio-transformation of a substrate into nitric oxide or "native" nitric oxide. The present invention preferably promotes therapeutic angiogenesis.

The present invention may also be useful in preventing, treating, arresting, or ameliorating disease conditions which are benefited by the bio-transformation of L-arginine into "native" nitric oxide through enzyme activation of NOS.

The present invention may also be useful in achieving a beneficial effect when treating disease conditions by increasing or maximizing the production of EDRF or EDNO, and reducing clinical endpoints to include mortality.

The present invention may also be useful in preventing, treating, or avoiding tachycardia and ischemia.

The present invention may also be useful in preventing, treating, arresting, or ameliorating reperfusion injury in subjects who have had abrupt restoration of blood flow.

In one embodiment of the present invention, a mixture of NOS agonists, preferably angiogenic growth factors, and biological equivalents of L-arginine are used for the treatment of hypertension, hypertensive heart disease, coronary heart disease, including arteriosclerosis, angina, myocardial infarction, coronary thrombosis, restenosis post angioplasty, and sudden death, as well as a wide range of cardiovascular disease (heart failure, stroke, and peripheral vascular diseases), and renovascular ischemia/hypertension.

In an alternative embodiment of the invention, therapeutically effective amounts of a precursor of EDNO and an agonist of NOS (preferably one of those cited in Table I herein) are combined prior to administration to a patient. In another embodiment of the invention, therapeutically effective amounts of a precursor of EDNO and an angiogenic growth factor are combined and administered.

In a preferred embodiment of the present invention, therapeutically effective amounts of L-arginine and therapeutically effective amounts of a macrophage secretory product are mixed at a physiologically acceptable pH.

Another embodiment of the present invention is a method for treating hypertension in a subject by vasodilation or vasorelaxation comprising: selecting a hypertensive subject; administering L-arginine and a NOS agonist (e.g., those listed in Table I), preferably angiogenic growth factors, to the subject; obtaining periodic blood pressure measurements of the subject; and continuing administration of L-arginine and the NOS agonist, preferably a secretory product, more preferably an angiogenic growth factor, even more preferably VEGF or bFGF angiogenic growth factors until a desirable blood pressure or therapeutic effect is detected in the subject. A desirable blood pressure in a hypertensive subject should ultimately be within the following ranges: systolic preferably in the range of 95–180 mmHg, more preferably in the range of 105–165 mmHg, and even more preferably in the range of 120 to 140 mmHg; and diastolic preferably in the range of 55–115 mmHg, more preferably in the range of 65–100 mmHg, and even more preferably in the range of 70 to 90 mmHg, and most preferably 75–85 mmHg. Under no circumstances should the systolic be permitted to go below 95 mmHg.

Another embodiment of the present invention is a method for preventing or treating cardiovascular disease in a non-hypertensive subject by vasodilation or vasorelaxation comprising: selecting a subject; administering to said subject a formulation comprising a mixture of an angiogenic growth factor and an endothelium dependent source or precursor of nitric oxide (e.g., L-arginine); obtaining periodic measurements of vasorelaxation on the subject and; continuing administration of the formulation until a desirable state of vasorelaxation or desirable therapeutic (e.g., angiogenic) effect is detected in the subject.

Yet another embodiment is a method for stimulating cNOS in a subject which comprises: selecting a subject; administering to said subject a formulation comprising a mixture of L-arginine and angiogenic growth factors so as to increase "native" NO production and reduce endpoints to include mortality.

DETAILED DESCRIPTION OF THE PREFERRED EMBODIMENTS

Figure 1:
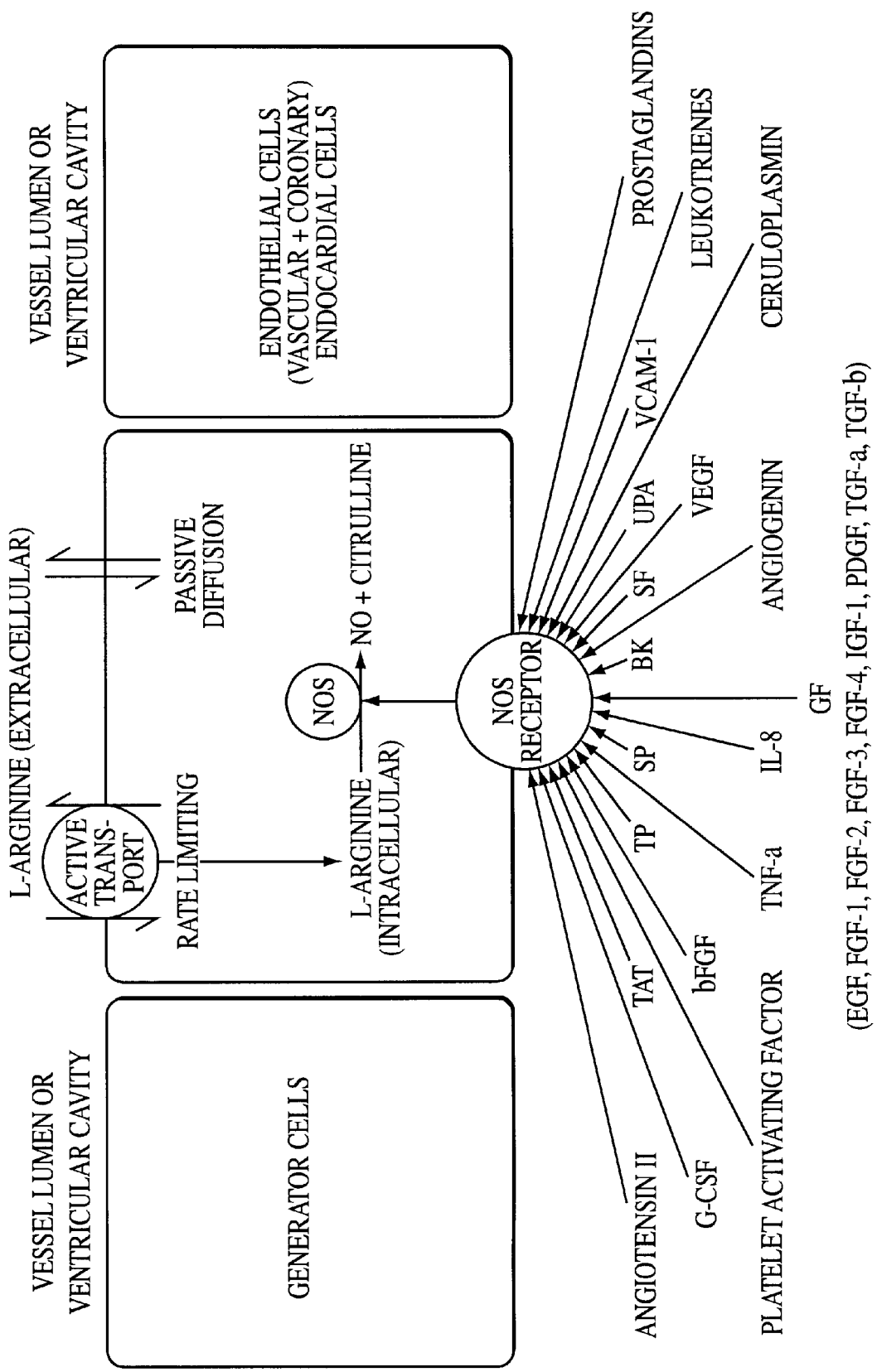
FIG. 1 is a schematic representation of NOS activation by select compounds and the conversion of L-arginine into NO.

Research into the area of NOS activation reveals a number of agonists of NOS. Interestingly, many of the NOS agonists have also been implicated in angiogenesis. Substance P ("SP"), a secretory product, is identified herein as a cNOS agonist. Other secretory products (e.g., those identified in "Macrophages and angiogenesis" by Sunderkotter et al. (J Leukoc Biol 1994 March; 55(3):410–22)) may also be expected to be agonists of NOS. Bradykinin ("BK"), a NOS agonist, has also been implicated as a possible angiogenic factor. Angiogenic growth factors like those identified in Table I stimulate the growth of new blood vessels (e.g., in vascular beds such as the coronary, peripheral, etc.) previously occluded with atherosclerotic obstructions. Angiogenic growth factors are proteins which were initially discovered as agents responsible for the growth of new blood vessels which maintain the growth and spread of cancerous tumors (neovascularization). Two of the angiogenic growth factors, vascular endothelial growth factor (VEGF) and basic fibroblastic growth factor (bFGF), have been infused into catheters, used at the time of generating coronary and peripheral arteriograms, and have resulted in the growth of significant new collateral blood vessels in the region of ischemia producing vascular atherosclerotic occlusions. In this way, the symptoms of ischemia are lessened. The term applied to this treatment approach is "therapeutic angiogenesis."

Like angiogenic agents Substance P and Bradykinin, VEGF and bFGF also appear to act as NOS agonists, specifically cNOS. It appears the resultant EDNO produced is in large part responsible for the new collateral vessel growth ("collateral") which in turn is responsible for the improvement in symptoms of ischemia seen in therapeutic angiogenesis. Furthermore, it has also been shown that the collateral responses to both VEGF and bFGF can be magnified significantly with L-arginine supplementation. Therefore, angiogenic growth factors, preferably VEGF and bFGF, appear to have dual applicability in the treatment of hypertension and cardiovascular diseases in that they both stimulate therapeutic angiogenesis and activity of Nitric Oxide Synthase. It also appears that the overall therapeutic angiogenic result with angiogenic growth factors is augmented to the extent they act as agonists of NOS. The fact that angiogenic growth factors are agonists or stimulators of nitric oxide synthase has important implications. Mixing angiogenic growth factors "in vitro" or "in vivo" with L-arginine may have an unforeseen beneficial effect that is associated with excess L-arginine providing additional substrate for NOS and the NOS being catalyzed to enzymatically increase the bio-transformation of L-arginine into nitric oxide (EDRF or EDNO) which would in turn amplify the overall therapeutic effect.

Stimulation of NOS by angiogenic growth factor(s) in the presence of excess L-arginine or other substrate precursor of native NO may be used to prevent, treat, arrest, or ameliorate any disease or condition which is positively affected by NO production. Such conditions include hypertensive cardiocerebrorenovascular diseases and their symptoms as well as non-hypertensive cardiocerebrorenovascular diseases. The mixture is particularly useful for subjects in need of native NO production for therapeutic angiogenesis. Application of such a mixture is beneficial for: (1) chronic stable angina; (2) unstable angina; (3) acute myocardial infarction; (4) hibernating myocardium; (5) stunned myocardium; (6) limitation of ventricular remodeling in post myocardial infarction and subsequent risk of congestive heart failure; (7) prophylaxis of recurrent myocardial infarction; (8) prevention of sudden death following myocardial infarction; (9) vasospastic angina; (10) congestive heart failure-systolic-seen in association with 1–6 above; (11) congestive heart failurediastolic-seen in association with 1–10 above and 12–15 below; (12) microvascular angina seen in association with 1–11 above and 15 and 16 below; (13) silent ischemia seen in association with 1–12 above and 15 and 16 below; (14) reduction of ventricular ectopic activity seen in association with 1–13 above and 15 below; (15) any or all of the above 1–14 states of ischemic myocardium associated with hypertensive heart disease and impaired coronary vasodilator reserve; (16) control of blood pressure in the treatment of hypertensive crisis, perioperative hypertension, uncomplicated essential hypertension and secondary hypertension; (17) regression of left ventricular hypertrophy seen in association with 15 and 16 above; (18) prevention and or regression of epicardial coronary arteriosclerosis seen in 1–17 above; (19) prevention of restenosis post angioplasty; (20) prevention and/or amelioration of free radical mediated reperfusion injury in association with 1–19 above; (21) use of the combination in the prevention of myocardial injury during cardioplegic arrest during coronary bypass or other open heart surgery i.e. use of the combination as a cardioplegic solution; (22) post transplant cardiomyopathy; (23) renovascular ischemia; (24) cerebrovascular ischemia (TIA) and stroke); (25) pulmonary hypertension; and (26) peripheral vascular disease (claudication).

Vascular smooth muscle cells are located mainly in veins, arteries, and coronary arteries. The following discussion focuses on smooth muscle and myocyte relaxation stimulated by vasodilators but should not be so limited. The present invention is useful when NO regulation is beneficial. As discussed above the Nitric Oxide Synthase in the cells is normally cNOS, the constitutive form of Nitric Oxide Synthase, and the generator cells are endothelial cells and the target cells are vascular smooth muscle cells. FIG. 1 is a schematic illustration of a proposed mechanism of action of preferred substances (e.g., angiogenic growth factors) and arginine and is not intended to imply any cellular relationship or geography of the various sites of action, but rather meant to illustrate their functional relationship. Although FIG. 1 list certain preferred agents as angiogenic agents, it is meant as a representative sampling of those listed in Table I. In FIG. 1 the abbreviations corresponding to Table I are used with SP representing Substance P and GF representing select Growth Factors.

The principle combination to be employed will be a mixture that involves therapeutic concentrations of L-arginine and therapeutic concentrations of angiogenic growth factor in water. Any pharmaceutical grade L-arginine will be sufficient and should be diluted preferably to 2.5–60% w/v (g/ml), more preferably to 5–45% w/v (g/ml), even more preferably between 7.5–30% w/v (g/ml), even more preferably to 10–15% w/v (g/ml), and most preferably 10% w/v (g/ml) L-arginine. The typical doses anticipated will be 30 grams of L-arginine in sterile water (Total Volume 300 cc). L-arginine is anticipated eventually to be approximately 10:1 to about 25:1 of the hydrochloride salt to L-arginine as a base, and even more preferably 15:1 to about 20:1 hydrochloride salt to base, and most preferably 15:1 hydrochloride salt to base. In this example 28 to 29 grams will be the hydrochloride salt and 1 to 2 grams of L-arginine will be base.

In the preferred embodiment discussed herein, L-arginine is used in conjunction with any of the family of those substances known as angiogenic growth factors. However, those particular angiogenic growth factors most preferred for use in conjunction with the present formulation are selected from the group consisting of VEGF and bFGF and even more preferably VEGF. Any of the agonists of Table I may be suitable candidates for use in combination with L-arginine.

As part of a "mixture", the angiogenic growth factor is included together with L-arginine and clinically effective weight ratios of between 1:2 to 1:150. Even more particularly, the ratio of the angiogenic growth factor to L-arginine in the formulation is between 1:5 to 1:100. The most preferred embodiment of the "mixture" the ratio of angiogenic growth factor, more preferably VEGF or bFGF, to L-arginine is 1:50. VEGF can be obtained from Genentech (South San Francisco, Calif.) and bFGF can be obtained from R&D Systems (Minneapolis, Minn.). The range of ratios of an angiogenic growth factor to L-arginine may be employed with virtually any of the angiogenic growth factors.

Where the particular angiogenic growth factor is VEGF the ratio of VEGF to L-arginine is preferably within the range 1:2 to 1:50, Wt/Wt. For example, VEGF/L-arginine at a ratio of 1:2 would include 40 mg/day VEGF with 80 mg/day L-arginine. Where the ratio of VEGF/L-arginine is at a ratio of 1:20, for example, 20 mg/day VEGF would be administered with 400 mg/day L-arginine. Weight ratio of ingredients described herein in regard to VEGF or bFGF are applicable for any of the agents listed in Table I. The amounts above have been found to be effective, however, each route of administration (i.e. IV, oral, transdermal, intracoronary, intra-arterial, etc.) may vary in their requirements.

Even more particularly, the presently disclosed "mixtures" may be described in terms of their relative concentrations (grams) administered as part of a continuous intracoronary, intra-arterial, intravenous and intrapericardial infusions. In one particular embodiment, the formulation is administered as mixtures of growth factors with L-arginine encased in liposomes so as to provide maximum retention time of the mixture in any given vascular bed being perfused by a catheter delivering the growth factor/L-arginine angiogenic mixture. In some cases the liposomes containing the mixture of growth factors and L-arginine may also contain genetic material which will code for the synthesis of the growth factor following transfection of the genetic material into the surrounding tissue of the vascular bed. In some cases pellets containing the aforementioned mixtures may be directly implanted into the myocardium at the time of coronary bypass graft surgery. In yet another case, a therapeutic mixture of L-arginine and an angiogenic growth factor are repeatedly infused into the pericardial space via an indwelling infusion catheter.

By way of example only, Table I presents a listing of several agents, most of which are angiogenic growth factors. These substances vary in their potency and their abilities to activate nitric oxide synthase and stimulate therapeutic angiogenesis.

TABLE I

| EGF (epidermal growth factor) | TGF-α (transforming growth factor-α) | Substance P |
|---|---|---|
| FGF-1 (fibroblast growth factor-1; aFGF) | TGF-β (transforming growth factor-β) | TAT (HIV-1 transactivating protein) |
| FGF-2 (fibroblast growth factor-2; bFGF) | TNF-α (tumor necrosis factor-α) | UPA (urokinase) |
| FGF-3 (fibroblast growth factor-3; int-2) | TP (thymidine phosphorylase; also called platelet-derived endothelial cell growth factor [PD-ECGF]) | VCAM-1 (vascular cell adhesion molecule) |

TABLE I-continued

| | | |
|---|---|---|
| FGF-4 (fibroblast growth factor-4; hst-1, K-FGF) | VEGF (vascular endothelial growth factor; vascular permealbility factor [VPF]; vasculotropin) | Lactate |
| Bradykinin (BK) | Angiogenin | Hyaluronan fragments |
| G-CSF (granulocyte colony-stimulating factor) | Angiotensin II | Erucamide |
| IGF-1 (insulin-like growth factor-1) | Ceruloplasmin | Leukotrienes $C_4$ and $D_4$ |
| IL-8 (interleukin-8) | Polyamines | $PGE_1$, $PGE_2$, (prostaglandins $E_1$, $E_2$) |
| PDGF (platelet-derived growth factor) | Platelet activating factor | Estrogen |
| SF (scatter factor; same as hepatocyte growth factor, [HGH]) | Proliferin | Nicotinamide |

Also specifically within the scope of those agents listed in Table I are their bio-active metabolites. Any one or several of those angiogenic growth factor compounds listed in Table 1 may be mixed with L-arginine or substrate precursor to endogenous nitric oxide to provide a therapeutically effective treatment for a patient.

While not wishing to be bound by theory, it is now believed that angiogenic agents have a stimulating effect on cNOS, and furthermore, that this action to stimulate cNOS is involved in the angiogenic response seen with growth factors. Thus, angiogenic growth factors and L-arginine appear to have a heretofore unexpected additive and/or synergistic effect on cNOS stimulation. The stimulation of cNOS may be a result of cNOS having a unique receptor site for angiogenic growth factors or angiogenic growth factors may initiate a cascade of events which stimulate NOS. Administering the two also provides adequate substrate for cNOS processing of L-arginine since the L-arginine is added in excess while at the same time stimulation the enzymatic activity of NOS. Whether it is a synergistic effect or additive effect, what is clear is that "mixing" a precursor substrate of "native" nitric oxide with angiogenic agents (e.g., VEGF and bFGF) results in a heretofore unexpected increase in NO production and angiogenesis. While not wishing to be bound by theory, growth factors appear to stimulate cNOS in much the same way as other NOS agonist and cNOS stimulation in turn stimulates angiogenesis.

By way of example, a therapeutic mixture, as previously described, of L-arginine and VEGF is infused into the coronary arteries of a patient with chest pain at the time of a coronary arteriogram which reveals multiple diffuse arthrosclerotic obstructive lesions which are amenable to treatment with bypass surgery or angioplasty. The treatment results in improvement in collateral blood flow and a decrease in the severity and frequency of angina attacks over the next 6 to 12 months.

The methods of the present invention involve administering to a mammalian host, preferably a human host, pharmacologically effective amounts of arginine and angiogenic growth factor. The agents may be combined in vitro before administration or separately administered, either concurrently or simultaneously, with administration generally taking place up to 24 hours before or after the administration of the other biological active agent(s).

The administration(s) may take place by any suitable technique, including oral, subcutaneous and parenteral administration, preferably parenteral or oral. Examples of parenteral administration include intravenous, intra-arterial, intramuscular, and intraperitoneal. The dose and dosage regimen will depend mainly on whether the inhibitors are being administered for therapeutic or prophylactic purposes, separately or as a mixture, the type of biological damage and host, the history of the host, and the type of inhibitors or biologically active agent. The amount must be effective to achieve an enhanced therapeutic index. It is noted that humans are generally treated longer than the mice and rats with a length proportional to the length of the disease process and drug effectiveness. The doses may be single doses or multiple doses over a period of several days. Therapeutic purposes is achieved as defined herein is when the treated hosts exhibit improvement against disease or infection, including but not limited to improved survival rate, more rapid recovery, or improvement or elimination of symptoms. If multiple doses are employed, as preferred, the frequency of administration will depend, for example, on the type of host and type of cancer, dosage amounts, etc. The practitioner may need to ascertain upon routine experimentation which route of administration and frequency of administration are most effective in any particular case.

Compounds and agents (e.g., both L-arginine and angiogenic growth factors) of the present invention, in conjunction with a pharmaceutically acceptable carrier, may be used for any of the therapeutic effects, discussed above. Such compositions may be in the form of an agent(s) in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones. Pharmaceutically-acceptable carriers may also be comprised of excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.) hereby incorporated herein by reference in its entirety.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound. i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxyrnethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. Such labeling would include amount, frequency, and method of administration.

The therapeutically effective dose of specific angiogenic growth factors can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Although the preferred methods have been described in detail, it should be understood that various changes, substitutions, and alterations can be made in the present invention as defined by the claims appended hereto. For example, the aforementioned therapeutic mixture of L-arginine and VEGF may alternatively be infused into a catheter used to diagnose peripheral vascular disease in patients suffering from claudication. The present invention is to be defined only by the claims attached hereto.

What is claimed is:

1. A therapeutic mixture comprised of an angiogenic growth factor and a biological equivalent of L-arginine, said angiogenic growth factor being selected from the group consisting of: EGF, TGF-α, TGF-β, FGF-1, FGF-2, FGF3, FGF-4, and IGF-1.

2. The therapeutic mixture of claim 1, wherein said biological equivalent of L-arginine.

3. The therapeucic mixture of claim 2, wherein said L-arginine is L-arginine hydrochoride.

4. The therapeutic mixture of claim 2, wherein said L-arginine is in excess of said angiogenic growth factor.

5. The therapeutic mixture of claim 1, wherein the mixture is formulated in a form of administration selected from the group consisting of intravenous, buccal, intracoronary, intraarterial, intrapericardial, intramuscular, tropical, intranasal, rectal, sublingual, oral, subcutaneous, patch and inhalation.

6. The therapeutic mixture of claim 1, wherein said biological equivalent of L-arginine and said angiogenic growth factor are mixed in vivo.

7. A therapeutic composition comprised of:
 a biological equivalent of L-arginine; and
 vascular endothelial growth factor (VEGF).

8. The composition of claim 7, wherein said biological equivalent of L-arginine is L-arginine.

9. The composition of claim 8, wherein said L-arginine; is L-arginine hydrochloride.

10. The composition of claim 7, wherein the composition is formulated in a form of administration selected from the group consisting of intravenous, buccal, intracoronary, intraarterial, intrapericardial, intramuscular, tropical, intranasal, rectal, sublingual, oral, subcutaneous, patch, and inhalation.

11. A composition comprised of:
 a biological equivalent of L-arginine; and
 basic fibroblactic growth factor (bFGF).

12. The composition of claim 11, wherein said biolohical equivalent of L-arginine is L-arginine.

13. The composition of claim 12, wherein said L-arginine is L-arginine hydrochloride.

14. The composition of claim 11, wherein the composition is formulated in a form of administration selected from the group consisting of intravenous, buccal, intracoronary, intraarterial, intrapericardial, intramuscular, topical, intranasal, rectal, sublingual, oral, subcutaneous, patch and inhalation.

* * * * *

UNITED STATES PATENT AND TRADEMARK OFFICE
CERTIFICATE OF CORRECTION

PATENT NO. : 6,239,172 B1
DATED : May 29, 2001
INVENTOR(S) : Kaesemeyer

Page 1 of 1

It is certified that error appears in the above-identified patent and that said Letters Patent is hereby corrected as shown below:

Claim 1,
Line 4, delete "FGF3" and insert therefore -- FGF-3 --.

Claim 2,
Line 2, after "L-arginine" insert -- is L-arginine -- to the end of the claim.

Claim 5,
Line 4, delete "tropical" and insert therefor -- topical --.

Claim 10,
Line 4, delete "tropical" and insert therefore -- topical --.

Claim 11,
Line 3, delete "fibroblactic" and insert therefore -- fibroblastic --.

Claim 12,
Line 1, delete "biolohical" and insert therefore -- biological --.

Signed and Sealed this

Sixteenth Day of April, 2002

Attest:

JAMES E. ROGAN
*Director of the United States Patent and Trademark Office*

*Attesting Officer*